United States Patent
Ouafik et al.

(10) Patent No.: US 9,028,818 B2
(45) Date of Patent: May 12, 2015

(54) ANTIBODIES BINDING TO ADRENOMEDULLIN RECEPTORS AND USES THEREOF AS DRUGS

(75) Inventors: L'Houcine Ouafik, Marseilles (FR); Kamel Mabrouk, Les Pennes Mirabeau (FR); Itidal Kaafarany, Tarbes (FR); Pierre-Marie Martin, Marseilles (FR)

(73) Assignees: Universite d'Aix-Marseille, Marseille Cedex (FR); Assitance Publique Hôpitaux de Marseille, Marseille Cedex (FR)

( * ) Notice: Subject to any disclaimer, the term of this patent is extended or adjusted under 35 U.S.C. 154(b) by 93 days.

(21) Appl. No.: 13/056,963

(22) PCT Filed: Jul. 31, 2009

(86) PCT No.: PCT/FR2009/000964
§ 371 (c)(1),
(2), (4) Date: Aug. 22, 2011

(87) PCT Pub. No.: WO2010/012911
PCT Pub. Date: Feb. 4, 2010

(65) Prior Publication Data
US 2011/0293634 A1 Dec. 1, 2011

(30) Foreign Application Priority Data

Jul. 31, 2008 (FR) ..................... 08 04382

(51) Int. Cl.
| | | |
|---|---|---|
| A61K 39/00 | (2006.01) | |
| A61K 39/395 | (2006.01) | |
| C07K 16/00 | (2006.01) | |
| C07K 16/28 | (2006.01) | |
| C07K 16/30 | (2006.01) | |

(52) U.S. Cl.
CPC ........... C07K 16/28 (2013.01); *A61K 2039/507* (2013.01); C07K 16/30 (2013.01); *C07K 2317/73* (2013.01)

(58) Field of Classification Search
None
See application file for complete search history.

(56) References Cited

FOREIGN PATENT DOCUMENTS

WO WO 2007/045927 A2 4/2007

OTHER PUBLICATIONS

Fernandez-Sauze et al. 2004. Int. J. Cancer 108:797-804.*
Nikitenko et al. 2002. Am. J. Pathol. 160:1-7.*
Kaafarani et al. 2009. FASEB J. 23:3424-3435.*
Ouafik et al. 2002. Am. J. Pathol. 160:1279-1292.*
Gura, Science Nov. 7, 1997: vol. 278. No. 5340, pp. 1041-1042.*
Leaf C. Health Administrator vol. XVII, No. 1: 172-183, 2005.*
Expert Scientific Group on Phase One Clinical Trials Final Report Nov. 30, 2006, pp. C1, C35-C38.*
Cancer Drug Design and Discovery Neidle, Stephen, ed. Elsevier/Academic Press, 2008, pp. 427-431.*
Kamb, Nature Reviews Drug Discovery 4, 161-165 Feb. 2005.*
Roberts et al., JAMA 292(17): 2130-2140 (2004).*
Kola et al, 2004. Nature Reviews Drug Discovery 3, 711-715.*
Abasolo, I. et al. 2004 "Adrenomedullin inhibits prostate cancer cell proliferation through a cAMP-independent autocrine mechanism" *Biochemical and Biophysical Research Communications* 322(3):878-886.
Fernandez-Sauze, S. et al. 2004 "Effects of adrenomedullin on endothelial cells in the multistep process of angiogenesis: involvement of CRLR/RAMP2 and CRLR/RAMP3 receptors" *International Journal of Cancer* 108(6):797-804.
Ishikawa, T. et al. 2003 "Adrenomedullin antagonist suppresses in vivo growth of human pancreatic cancer cells in SCID mice by suppressing angiogensis" *Oncogene* 22(8):1238-1242.
Nakamura, M. et al. 2006 "Adrenomedullin: a tumor progressionfactor via angiogenic control" *Current Cancer Drug Targets* 6(7):635-643.

* cited by examiner

*Primary Examiner* — Shulamith H Shafer
(74) *Attorney, Agent, or Firm* — Knobbe, Martens, Olson & Bear, LLP

(57) ABSTRACT

The invention relates to antibodies binding to the proteins forming adrenomedullin receptors, and to the uses thereof as a drug.

15 Claims, 10 Drawing Sheets

A

B

A

B

A

B

ANTIBODIES BINDING TO ADRENOMEDULLIN RECEPTORS AND USES THEREOF AS DRUGS

RELATED APPLICATIONS

This application is a U.S. National Phase of International Application No.: PCT/FR2009/000964, filed Jul. 31, 2009, designating the U.S. and published on Feb. 4, 2010 as WO 2010/012911 A1, which claims the benefit of French Application No. 08 04382, filed Jul. 31, 2008.

FIELD OF THE INVENTION

The present invention relates to the field of antibodies used as a medicament, intended in particular for the treatment of tumors. More particularly, the invention relates to antibodies which bind to the proteins forming adrenomedullin receptors and to the uses thereof as a medicament.

BACKGROUND OF THE INVENTION

Angiogenesis is the fundamental process by which new blood vessels are formed. The process comprises the migration of vascular endothelial cells into a tissue, followed by the organization of said endothelial cells into vessels.

Angiogenesis plays a determining role in tumor growth and the development of metastases. In healthy tissues, an equilibrium exists between pro-angiogenic factors and anti-angiogenic factors; these factors being expressed or disregulated in tumor processes (Hanahan and Folkman, *Cell,* 1996, 86:353-364). Beyond a certain tumor volume, the growth of the tumor requires the development of a neovascularization which will bring it the necessary oxygen and nutrients. Tumor cells themselves secrete angiogenic factors and stimulate their microenvironment in order to increase the bioavailability of the factors necessary for the development of tumor angiogenesis.

The existence of a highly developed vascular network in tumors has been known for many years. As early as 1971, Folkman (*N Engl J. Med.,* 1971, 285:1182-6) put forward the hypothesis that tumor growth was dependent on neovascularization (angiogenesis) and that the change from the latent phase to the aggressive phase was directly controlled by neovascularization, by means of diffusible substances originating from the tumor.

The control of angiogenesis involves several factors. It is triggered by a disequilibrium in the balance between the pro-angiogenic factors (for example, vascular endothelial growth factor (VEGF), fibroblast growth factor (FGF), epidermal growth factor (EGF), platelet derived growth factor (PDGF), angiopoietins, or else angiogenin) and the anti-angiogenic factors (for example, endostatin and angiostatin, thrombospondins, vasostatin, prolactin, or else interferons).

Tumor cells, but also the inflammatory cells, macrophages, lymphocytes and myofibroblasts present in the tumor microenvironment, secrete angiogenic factors.

It is conventional to distinguish two phases during angiogenesis. The first phase is an induction phase which involves destabilization of the pre-existing tissue vascularization and destruction of the basal membrane surrounding the pre-existing vessels, and which requires the proliferation and migration of endothelial cells, and also the differentiation thereof to give capillary structures. The second phase is a stabilization/maturation phase during which perivascular cells (pericytes) are recruited, resulting in stabilization of the neocapillaries, and during which a basal membrane is reconstituted (Hanahan and Folkman, 1996, cited above).

It is now well established that the growth of a tumor and the formation of metastases are directly dependent on angiogenesis, suggesting that the inhibition of angiogenesis may represent an effective approach for preventing tumor progression and controlling metastatic diffusion.

Adrenomedullin (AM), isolated from human pheochromocytoma (cancer of the adrenal medulla), is a vasoactive peptide which acts locally as an autocrine/paracrine hormone and exerts multiple biological actions (Hinson et al., *Endocr Rev.,* 2000, 21:138-67; Caron and Smithies, *Proc Natl Acad Sci USA,* 2001, 98:615-619; Shindo et al., *Circulation,* 2001, 104:1964-1971).

Several studies have shown that adrenomedullin binding sites are present in the cells of most tissues, such as the heart, the kidney, the brain, the lung and the adrenal gland. Binding sites are also present in tumor stromal cells. A role for adrenomedullin in tumor growth has also been demonstrated (Ouafik et al., *Am J. Pathol.,* 2002, 160:1279-92; Martinez et al., *J Natl Cancer Inst,* 2002, 94:1226-37; Oehler et al., *Oncogene,* 2001, 20:2937-45; Ishikawa et al., *Oncogene,* 2003, 22:1238-1242).

This peptide may also play a positive role in the regulation of angiogenesis during vascular remodeling in response to ischemia, in the female reproductive system, during embryonic vascular development, and during the development and vascularization of the placenta.

Recently, several teams have demonstrated a role for adrenomedullin on endothelial cell proliferation, migration and invasion (Ouafik et al., 2002, cited above; Kim et al., *FASEB J.,* 2003, 17:1937-9; Fernandez-Sauze et al., *Int J Cancer,* 2004, 108:797-804).

It has been shown, by means of in vivo and in vitro angiogenesis tests, that adrenomedullin acts on one of the last steps of neovascularization which consists of the reorganization of endothelial cells into tubules, independently of VEGF (Fernandez-Sauze et al., 2004, cited above).

Several studies demonstrate that adrenomedullin has angiogenic properties in most tumors (breast, prostate, colon, lung, kidney, respiratory tracts, bladder) (Ouafik et al., 2002, cited above; Fernandez-Sauze et al., 2004, cited above; Nikitenko et al., *Br J Cancer,* 2006, 94:1-7). In heterozygous adrenomedullin+/−mice, tumor volume decreases compared with the wild-type mice (Iimuro et al., *Cir. Res.,* 2004, 95:415-423). This effect is associated with a reduction in neovascularization. Blocking the action of adrenomedullin with an antagonist (adrenomedullin$_{22-52}$) inhibits the growth of xenografted pancreatic tumors by destabilizing tumor vascularization (Ishikawa et al., *Oncogene,* 2003, 22:1238-1242). Similar effects have been observed in xenografts developed from glial tumor cells (Ouafik et al., 2002, cited above).

The discovery of the AMBP-1 (Adrenomedullin Binding Protein-1) serum protein suggests a regulation of the bioavailability of said adrenomedullin. AMBP-1 has been described and characterized as being human complement factor H. In general, binding proteins limit transport of the peptide in the interstitial space and access to its specific receptors. They also modulate the biological activity of the peptide and protect it against metabolic clearance by proteases, thus prolonging its half-life in the blood stream.

Adrenomedullin receptors (AMRs) are multiprotein complexes composed of the association of at least two proteins, CRLR (Calcitonin Receptor Like Receptor) and a RAMP protein (Receptor Actvity-Modifying Protein) (McLatchie et al., *Nature,* 1998, 6683:333-9).

The CRLR receptor was isolated in 1993 (Njuki et al., *Clin Sci.*, 1993 4:385-8; Chang et al., *Neuron.*, 1993, 6:1187-95). It comprises seven transmembrane G protein-coupled domains. The CRLR sequence was established in humans in 1996 (Aiyar et al., *J Biol. Chem.*, 1996, 19:11325-9) and in pigs in 1998 Elshourbagy et al., *Endocrinology*, 1998, 4:1678-83). CRLR belongs to GPCR (G-protein-coupled receptor) class II, a class which groups together receptors for peptides such as glucagon and glucagon-like peptides (GLPs), secretin, parathormone or calcitonin. GPCRs are polypeptide in nature and comprise an extracellular portion carrying the ligand binding site, a seven-helix transmembrane portion and an intercellular portion in contact with the G proteins which provide the transfer and amplification of the signal received by the receptor. Three extracellular loops (called E1, E2 and E3) and three intracellular loops (I1, I2 and I3) can be observed (Bockaert and Pin, *Embo J.*, 1999, 18:1723-1729). These proteins can be subject to post-translational modifications, such as N-glycosylation, or acetylation by lipid compounds sometimes forming a pseudo fourth intracellular loop (14) (Assie et al., *EMC-Endocrinologie*, 2004, 1:169-199).

For a few years, there was a certain amount of confusion regarding the exact nature of the adrenomedullin receptor owing to the homology of adrenomedullin with CGRP (Calcitonin Gene Related Peptide) and to it belonging to the calcitonin/CGRP/amylin peptide family. In 1998, McLatchie and collaborators (reference cited above) demonstrated that the CRLR receptor can generate two pharmacologically distinct receptors by association with a family of proteins, of 160 amino acids (14-21 Kda), with a single transmembrane domain, called RAMPs. CRLR is correctly functional only in the state of a dimer with a RAMP protein.

Three protein isoforms of RAMP exist: RAMP1, 2 and 3. These proteins have less than 30% sequence identity with one another, but have structural organization similarities. In humans, the genes encoding RAMP1, RAMP2 and RAMP3 are carried by chromosomes 2, 17 and 7, respectively. The RAMP proteins consist of a single transmembrane domain; the extracellular N-terminal end is relatively long and plays an important role in the specialization and the functionality of the receptor (CGRP or adrenomedullin) (Kuwasako et al., *J Biol. Chem.*, 2001, 275:29602-9).

Two essential functions are attributed to the RAMP proteins: receptor determination and intracellular transport.

Receptor determination: the fundamental role of RAMP proteins is to define the specificity of the ligand which interacts directly at the cell surface. RAMP1 presents CRLR as a mature glycoprotein so as to form the CGRP receptor. Likewise, RAMP2 and RAMP3 present CRLR as a mature glycoprotein so as to form the adrenomedullin receptors. Thus, the nature of the RAMP proteins present in a cell type, the protein interactions which are established between the various partners (CRLR, RAMP1, RAMP2, RAMP3) and the proportion of each of the proteins allow the cells to respond specifically to various neuropeptides (Bühlmann et al., *FEBS Lett.*, 2000, 486:320-4; Chakravarty et al., *Br J. Pharmacol.*, 2000, 130:189-95).

Intracellular transport: CRLR requires the coexpression of the RAMP proteins for its transport to the cytoplasmic membrane (Sexton et al., *Cell Signal*, 2001, 13:73-83). It is also reciprocally the case: the RAMP proteins need CRLR for their translocation to the cell surface (Flahaut et al., *J Biol. Chem.*, 2002, 277:14731-7).

The growth of solid tumors is controlled by intratumor mechanisms and by interactions between the tumor and the surrounding tissue. In the quiescent phase, few vessels are detected. On the other hand, during the growth phase and during the invasive phase, there is an enormous amount of angiogenesis. A close correlation exists between tumor growth and the number of intratumor capillaries. Thus, angiogenesis-dependent solid tumors exhibit a latent pre-angiogenic phase and an aggressive angiogenic phase.

The treatment of tumors, in particular solid tumors, is based mainly on surgery, radiotherapy and chemotherapy. However, despite the progress obtained in these fields and the encouraging results, it proves to be essential to have new anticancer agents with a mechanism of action that is different from the available anticancer agents, inter alia in the field of targeted therapeutics, for increasing the efficacy of the treatment, in particular in the case of the appearance of resistance to a treatment and/or of adverse effects which are too great.

Alongside therapies aimed at the destruction of proliferative cells (chemotherapy) and hormone therapy in the context of hormone-dependent cancers (breast, prostate), targeted therapeutics are aimed at all the pathways which contribute to tumor development, such as proliferation signals, the cell cycle, apoptosis, invasion or angiogenesis (Folkman, *Nat Rev Drug Discov.*, 2007, 6:273-286; Neri and Bicknell, *Nat Rev Cancer*, 2005, 5:436-446).

The presence of tumor neoangiogenesis associated with overexpression of the mRNAs of angiogenic factors such as VEGF and FGF-2 has resulted in the development of inhibitors (specific antibodies, antisense oligonucleotides, pharmacological inhibitors) by several pharmaceutical companies. A certain number of molecules, currently undergoing clinical trials, are involved in therapeutic protocols jointly with conventional treatments.

However, it is known that the use of anti-VEGF antibodies for treating tumors, even if it gives good results (rapid arrest of tumor growth), has considerable toxic effects. In addition, a recurrence (resumption of tumor growth) can occur in the more or less short term after treatment has stopped. Furthermore, these treatments are aimed at the endothelial cells, but not all the cells of the tumor stroma that are involved in establishing a functional neoangiogenesis.

There still remains therefore a need for effective treatments aimed at blocking, or even inhibiting, tumour growth and/or at regressing tumor size.

In this context, the targeting of adrenomedullin via its receptors for therapeutic purposes constitutes a relevant approach owing to its mechanism of action which relates to the endothelial cells, but also, unlike VEGF, to the tumor cell and to all the cells of the stroma, particularly the pericytes.

Thus, Fernandez-Sauze et al. (2004, cited above) have shown that, in vitro, mixtures of anti-CRLR/anti-RAMP2 polyclonal antibodies, on the one hand, and anti-CRLR/anti-RAMP3 polyclonal antibodies, on the other hand, inhibit the specific binding of adrenomedullin to its receptor on several cell types and block the formation of vascular tubes. More recently, it has been described, in International Application WO 2007/045927, that pharmaceutical compositions comprising antibodies which bind specifically to the RAMP2 or RAMP3 human proteins can be of use for treating or preventing cancer, via, for example, the inhibition of angiogenesis or of the proliferation of cancer cells.

The inventors have prepared antibodies which bind to the proteins that form adrenomedullin receptors and have shown, surprisingly, that a mixture of at least three antibodies which bind to three different proteins forming adrenomedullin receptors, more particularly the hCRLR, hRAMP2 and hRAMP3 proteins, exhibit an antitumor efficacy in vitro and/or in vivo which is significantly greater compared with the use of a single anti-CRLR, anti-RAMP2 or anti-RAMP3 antibody, or even compared with the use of a mixture of two anti-CRLR/anti-RAMP2 or anti-CRLR/anti-RAMP3 antibodies.

The subject of the present invention is therefore a mixture of at least three antibodies and/or fragments of said antibodies which bind to three of the proteins forming adrenomedullin receptors, each antibody and/or antibody fragment binding to a different protein, for use as a medicament.

BRIEF DESCRIPTION OF THE DRAWINGS

Other aspects and advantages of the present invention will emerge on reading the examples which follow, which should be considered as nonlimiting illustrations, and also the appended figures.

DETAILED DESCRIPTION OF THE PREFERRED EMBODIMENT

Figure 1:
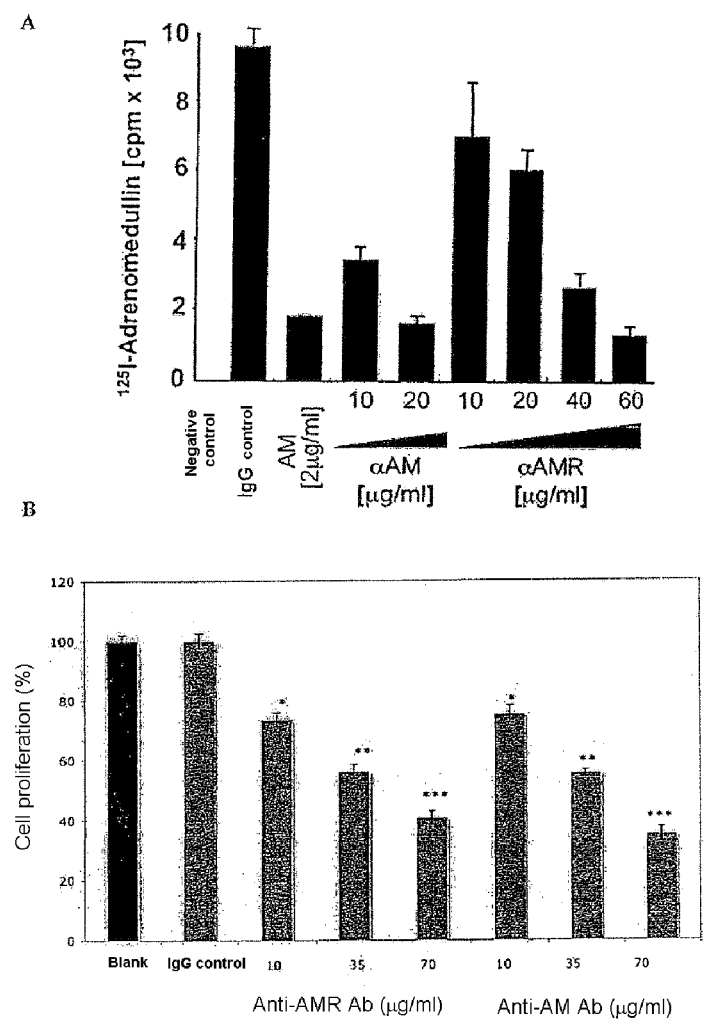
FIG. 1: Study of cell proliferation in vitro. A. Effect of the anti-adrenomedullin receptor (mixture of anti-CRLR, anti-RAMP2 and anti-RAMP3 antibodies) and anti-adrenomedullin antibodies on the binding of adrenomedullin, labeled with radioactive iodine 125, to the membranes of U87 glial cells. With 60 µg of anti-adrenomedullin receptor antibody, the inhibition of binding of the $I^{125}$-AM is greater than with 10 µg of antibody. B. In the glioblastoma-derived line (U87), treatment for 6 days with the anti-AM antibody or the mixture of anti-CRLR, anti-RAMP2 and anti-RAMPS antibodies inhibits cell proliferation by 30% to 60% in a dose-dependent manner, compared with the control cells incubated in the presence of the rabbit pre-immune serum. ANOVA Test: , $p<0.01$; *, $p<0.001$.

The expression "proteins forming adrenomedullin receptors" is intended to mean the proteins of which the association forms the adrenomedullin receptors (Hinson et al., 2000, cited above; McLatchie et al., 1998, cited above). Preferably, said proteins are mammalian proteins, and more preferably proteins of human origin. By way of nonlimiting examples of proteins forming adrenomedullin receptors, mention may be made of the following proteins: the CRLR (calcitonin receptor like receptor) protein, the associated RAMP (receptor activity-modifying protein) proteins, such as the RAMP2 and RAMP3 proteins. The amino acid sequences of the CRLR, RAMP2 and RAMP3 proteins of human origin are respectively available under accession numbers gi|5031621, gi|118572585 and gi|5032023 in the Genbank database.

According to one preferred embodiment of the present invention, the three proteins forming adrenomedullin receptors are the CRLR protein and the RAMP2 and RAMP3 proteins.

According to another advantageous embodiment of the present invention, said antibodies and antibody fragments bind to an extracellular domain of the proteins forming adrenomedullin receptors concerned, and more particularly to the peptides of sequences SEQ ID No. 1 or 2 for the anti-CRLR antibodies, to the peptides of sequences SEQ ID No. 3 or 4 for the anti-RAMP2 antibodies and to the peptides of sequences SEQ ID No. 5 or 6 for the anti-RAMP3 antibodies.

The invention encompasses natural, recombinant or synthetic polyclonal or monoclonal antibodies, chimeric antibodies such as humanized antibodies, and also fragments thereof (for example: Fab, Fv, scFv) which have retained their ability to bind to said proteins, or more particularly to the peptides of sequences SEQ ID No. 1 or 2 for the anti-CRLR antibodies, to the peptides of sequences SEQ ID No. 3 or 4 for the anti-RAMP2 antibodies and to the peptides of sequences SEQ ID No. 5 or 6 for the anti-RAMP3 antibodies.

Said antibodies or antibody fragments are adrenomedullin receptor antagonsists, i.e. they block (or inhibit) the binding of adrenomedullin to its receptors in a dose-dependent manner.

The term "recombinant antibody" is intended to mean an antibody produced by genetic engineering (e.g., cloning, amplification).

The term "synthetic antibody" is intended to mean an antibody produced by enzymatic and/or chemical synthesis.

The antibodies according to the present invention may be obtained by immunization of an animal with a protein forming adrenomedullin receptors, a peptide comprising or consisting of a fragment of at least 20, preferably 22 amino acids of said protein, or a peptide comprising or consisting of a peptide derived from said fragment.

The expression "peptide derived from a fragment of a protein forming adrenomedullin receptors" is intended to mean a fragment of said protein in which one or more amino acid residues has (have) been deleted and/or one or more amino acid residues has (have) been substituted with a natural or unnatural amino acid residue or an amino acid residue of D-type or beta-type configuration, and/or one or more natural or unnatural amino acid residues has (have) been inserted therein, and/or one or more amide bonds has (have) been modified, it being understood that said peptide derived from a fragment of a protein forming adrenomedullin receptors retains its ability to induce the production, by said animal, of antibodies which bind it to said protein.

Advantageously, each of the following peptides can be used to immunize an animal in order to obtain an antibody according to the present invention:

peptides derived respectively from fragments S27-K51 and P89-R119 of the hCRLR protein:

SPEDSIQLGVTRNKIMTAQYEAYQK,      (SEQ ID No. 1)

PDYFQDFDPSEKVTKIADQDGNWFRHPASNR,  (SEQ ID No. 2)

peptides derived respectively from fragments K59-K81 and R91-R118 of the hRAMP2 protein:

KNYETAVQFAWNHYKDQMDPIEK,        (SEQ ID No. 3)

RPYSTLRDALEHFAELFDLGFPNPLAER,   (SEQ ID No. 4)

peptides derived respectively from fragments L34-K55 and G91-E112 of the hRAMP3 protein:

LERLPLAGKAFADMMGKVDVWK,         (SEQ ID No. 5)

GFITGIHRQFFSNATVDRVHLE.         (SEQ ID No. 6)

The amino acid residue denoted "A" corresponds to an alanine residue obtained by substitution of a cysteine residue present in the peptide sequence of the natural hCRLR, hRAMP2 or hRAMP3 proteins. Substituting the cysteine residue with an alanine residue makes it possible to obtain a well-characterized linear peptide sequence and avoids obtaining mixtures of peptides comprising dimers (by formation of interchain disulfide bridges).

Preferably, the animal immunized is a mammal, such as, for example, horse, goat, rabbit, rat or mouse, and more preferably rabbit or mouse.

According to another particular embodiment of the present invention, said antibodies are polyclonal antibodies, preferably rabbit polyclonal antibodies.

It is possible for the mixture of antibodies and/or antibody fragments according to the present invention to comprise both polyclonal antibodies and monoclonal antibodies as defined above.

In said mixture, said antibodies and/or antibody fragments may be present in any ratio with respect to one another, such as, for example, a ratio of between 0.1 and 10. A preferred ratio is a ratio of 1.

Advantageously, said medicament is intended for the preventive or curative treatment of tumors, preferably those for which vascularization is necessary for their growth, more particularly for solid tumors.

The term "solid tumors" is intended to mean, for example, central nervous system tumors, such as gliomas (for example glioblastomas), or prostate, liver, bone, lung, colon, skin or else kidney tumors.

The invention also encompasses fast-growing tumors and also tumors in the therapeutic escape phase.

The use, as a medicament, of the antibodies and/or antibody fragments according to the present invention may be simultaneous, separate or sequential over time, in particular during a treatment in an individual suffering from cancer.

The subject of the present invention is also a mixture of at least three antibodies and/or antibody fragments as defined above, for the preparation of a medicament intended for the treatment of tumors, preferably solid tumors.

The subject of the present invention is also a pharmaceutical composition comprising at least three antibodies and/or antibody fragments as defined above, and at least one pharmaceutically acceptable vehicle.

By way of nonlimiting examples of a pharmaceutically acceptable vehicle, mention may be made of dispersants, solubilizing agents, stabilizers, preservatives, etc. Pharmaceutically acceptable vehicles that can be used in (liquid and/or injectable and/or solid) formulations are in particular methylcellulose, hydroxymethyl-cellulose, carboxymethyl-cellulose, cyclodextrins, polysorbate 80, mannitol, gelatin, lactose, plant or animal oils, acacia, etc.

Said medicament or said pharmaceutical composition may be in the form of a physiological, isotonic and buffered saline solution compatible with pharmaceutical use and known to those skilled in the art.

Said medicament or said pharmaceutical composition may be formulated in any pharmaceutically acceptable form, for instance in the form of an injectable suspension, of gels, oils, tablets, suppositories, gelatin capsules, capsules, etc., optionally used by means of galenical forms or of devices which provide sustained and/or delayed release. For this type of formulation, an agent such as cellulose, carbonates or starches is advantageously used.

The amount of antibody and/or antibody fragment used as a medicament according to the invention or present in the pharmaceutical composition according to the invention may be modulated so as to obtain a circulating level of active ingredient (in a physiological fluid such as blood) necessary for obtaining the therapeutic effect desired for a particular individual. The amount chosen will depend on many factors, in particular on the route of administration, on the duration of administration, on the time at which the administration is carried out, on the rate of elimination of the compound, on the various product(s) used in combination with said medicament or said pharmaceutical composition, on the age, the weight and the physical condition of the patient, and also on the medical history of said patient, and on any other information known in medicine.

The prescription by the treating physician may begin at doses below those generally used for antibodies, and then these doses will be gradually increased in order to have better control of the appearance of possible side effects.

In general, the daily dose of the compound will be the minimum dose for obtaining the therapeutic effect. This dose will depend on the various factors previously mentioned. The doses will in general be between 0.1 and 100 mg per kg per day for humans, and preferably between 4 and 25 mg per kg and per day, and even more advantageously between 7 and 14 mg per kg and per day.

If necessary, the daily dose can be administered in two, three, four, five, six or more intakes per day or via multiple subdoses administered at suitable intervals during the day.

Advantageously, the composition according to the present invention is preferably administered parenterally or directly, if this is possible, into the tumor (intratumoral administration).

The medicament or the pharmaceutical composition according to the present invention can be used alone or in combination with at least one other therapeutically active compound, such as, for example, another anticancer compound. The use of said medicament or of said pharmaceutical composition, and of said therapeutically active compound, may be simultaneous, separate or sequential over time, in particular during a treatment of an individual suffering from cancer.

The subject of the present invention is also an antibody, preferably a polyclonal antibody, which binds to the extracellular domain of the CRLR protein and which can be obtained by immunization of an animal, preferably a rabbit, with a peptide chosen from the peptides of sequence SEQ ID No. 1 and SEQ ID No. 2, and the use thereof for detecting, in vitro, ex vivo or in vivo, in an animal, preferably a mammal, more preferably in humans, the CRLR protein.

The subject of the present invention is also an antibody, preferably a polyclonal antibody, which binds to the extracellular domain of the RAMP2 protein and which can be obtained by immunization of an animal, preferably a rabbit, with a peptide chosen from the peptides of sequence SEQ ID No. 3 and SEQ ID No. 4, and the use thereof for detecting in vitro, ex vivo or in vivo, in an animal, preferably a mammal, more preferably in humans, the RAMP2 protein.

The subject of the present invention is also an antibody, preferably a polyclonal antibody, which binds to the extracellular domain of the RAMP3 protein and which can be obtained by immunization of an animal, preferably a rabbit, with a peptide chosen from the peptides of sequence SEQ ID No. 5 and SEQ ID No. 6, and the use thereof for detecting in vitro, ex vivo or in vivo, in an animal, preferably a mammal, more preferably in humans, the RAMP3 protein.

The subject of the present invention is also a method for obtaining an antibody which binds to an extracellular domain of CRLR, characterized in that it comprises a step of immunizing an animal with a peptide chosen from the peptides of sequence SEQ ID No. 1 and SEQ ID No. 2, preferably SEQ ID No. 2.

The subject of the present invention is also a method for obtaining an antibody which binds to the extracellular domain of RAMP2, characterized in that it comprises a step of immunizing an animal with a peptide chosen from the peptides of sequence SEQ ID No. 3 and SEQ ID No. 4, preferably SEQ ID No. 4.

The subject of the present invention is also a method for obtaining an antibody which binds to the extracellular domain of RAMP3, characterized in that it comprises a step of immunizing an animal with a peptide chosen from the peptides of sequence SEQ ID No. 5 and SEQ ID No. 6, preferably SEQ ID No. 5.

EXAMPLE

I: Materials and Methods

I.1. Obtaining the Anti-Adrenomedullin Receptor Antibodies Immunizations

The anti-CRLR polyclonal antibodies were developed by injecting rabbits with the peptide sequences SEQ ID No. 1 or SEQ ID No. 2. The anti-RAMP2 polyclonal antibodies were produced by injecting rabbits with the peptide sequences SEQ ID No. 3 or SEQ ID No. 4. The anti-RAMP3 polyclonal antibodies were produced by injecting rabbits with the peptide sequences SEQ ID No. 5 or SEQ ID No. 6.

SEQ ID No. 1: SPEDSIQLGVTRNKIMTAQYEAYQK,

SEQ ID No. 2: PDYFQDFDPSEKVTKIADQDGNWFRHPASNR,

SEQ ID No. 3: KNYETAVQFAWNHYKDQMDPIEK,

SEQ ID No. 4: RPYSTLRDALEHFAELFDLGFPNPLAER,

SEQ ID No. 5: LERLPLAGKAFADMMGKVDVWK,

SEQ ID No. 6: GFITGIHRQFFSNATVDRVHLE.

The animals were immunized with the various peptides supplemented with Freund's adjuvant. Immunization booster injections were subsequently given every 3 weeks.

The nonimmune sera used as control (pre-immune) were collected from the same animals before the beginning of the injections.

Purification of Immunoglobulins (IgGs) and Assaying of Endotoxin

Polyclonal antibodies were purified by passing them over a gel of sepharose beads coupled to protein A (GE Healthcare) and eluted with 100 mM glycine, pH 3. The presence of endotoxin in the antibodies was verified using the LAL test (*Limulus Amebocyte* Lysate, Chambrex). The results show a tolerable level of endotoxin (<1.25 U) in the various antibody preparations and also in the pre-immune serum. The immunoglobulin concentration was calculated by the Pierce method (Bicinchoninic (BCA) Protein Assays; Smith et al., *Anal Biochem*, 1985, 150:76-85).

I.2. Cell Culture

The A498 and BIZ lines come, respectively, from DSMZ (Germany) and from the laboratory of Dr. Gogusev (Necker Hospital-Paris). The BIZ line is derived from a kidney cancer; it has a deletion of the 3p13-pter region and also other genetic modifications such as der(1) dup(1)(q21 qter)×2, der(1) t(1; 15)×2, der(13) t(1;13)×2. All the other cell lines come from the American Type Culture Collection (Rokville Md., USA). The cells which come from tumors or biopsies are maintained in a suitable medium according to the cell type (cf. Table 1 below), in a humid atmosphere composed of 5% $CO_2$ and 95% air at 37° C.

TABLE 1

Cells used which come from tumors or biopsies

| Name | Origin | Location | Trial in mice | Culture medium |
|---|---|---|---|---|
| A498 (tumor) | ATCC No.: HTB-44 DSMZ (Germany) man (52 years old) | kidney | + | MEM 2 mM glutamine 1.5 g/l sodium bicarbonate 1 mM sodium pyruvate 10% FBS |
| A549 (tumor) | ATCC No.: CCL-185 man (58 years old) | lung | + | DMEM 2 mM glutamine 10% FBS |
| BIZ (metastasis) | Dr. Gogusev INSERM U507-Necker Hospital-Paris | kidney | not tested | RPMI 2 mM glutamine 2.2 g/l sodium bicarbonate 10% FBS |
| Caki1 (metastasis) | ATCC No.: HTB-46 man (49 years old) | kidney | + | McCoy's5a 2 mM glutamine 2.2 g/l sodium bicarbonate 10% FBS |
| Caki2 (tumor) | ATCC No.: HTB-47 man (69 years old) | kidney | + | McCoy's5a 2 mM glutamine 2.2 g/l sodium bicarbonate 10% FBS |
| IGR-37 (tumor) | DSMZ No.: ACC 237 man (59 years old) | skin | + | MEM 2 mM glutamine 10% FBS |
| HT29 (tumor) | ATCC No.: HTB-38 woman (44 years old) | colon | + | DMEM 2 mM glutamine 10% FBS |
| MCF-7 (metastasis) hormone-sensitive | ATCC No.: HTB-22 woman (69 years old) | breast | + | DMEM/F-12 2 mM glutamine 16 ng/ml insulin 10% FBS |
| MDA-MB231 (metastasis) hormone-independent | ATCC No.: HTB-26 woman (51 years old) | breast | + | L-15 5 µg/ml insulin 2 mM glutamine 10% FBS |
| U87 (tumor) | ATCC No.: HTB-14 man (68 years old) | glioblastoma | + | MEM 2 mM glutamine 1 mM sodium pyruvate 10% FBS |

The media are renewed every two days; when the cells reach 90% confluence, they are detached with a solution of trypsin (0.25%) in Tris buffer (Gibco) for a few minutes at 37° C. The action of the enzyme is stopped by adding medium containing serum. The cells are seeded either in 75 $cm^2$ tubes or in multiwell plates, in their appropriate media.

I.3. Specificity of Binding of Adrenomedullin to its Own Receptors by Means of Binding Experiments The U87 glial tumor cells are seeded into 24-well plates (40 000 cells/well) and maintained in MEM in the presence of 10% fetal bovine serum (FBS) for 48 hours. They are washed in 1×PBS and preincubated for 30 min with MEM 0.1% BSA (bovine serum albumin) containing radioiodonated adrenomedullin (Amersham Biosciences GE) in a proportion of 100 000 cpm in the presence of an antibody mixture composed of the anti-CRLR, anti-RAMP2 and anti-RAMP3 antibodies. The anti-CRLR, anti-RAMP2 and anti-RAMP3 antibodies were produced in rabbits by injecting the peptide sequences SEQ ID No. 2, 3 and 5, respectively. After incubation for 1 hour at ambient temperature, the cells are placed on ice and rinsed twice with a 1×PBS-0.1% BSA solution kept at 4° C. The cells are solubilized with 0.2N sodium hydroxide. The bound $^{125}$I-AM is counted in a Riastar gamma counter (Packard Instrument Company).

I.4. In Vivo Studies

Animal Models

Athymic (nu/nu) Balb/C female mice and C57BL/6 mice (Harlan, France) that were 4-5 weeks old were used. They are kept under sterile conditions, at a stable temperature and with suitable feeds. The in vivo experiments begin only after a period of adaptation of the animals to their new climate (10-15 days after reception).

Development of Xenografts and Treatment of Animals

The various tumor lines, U87, A549 and HT29, were subcutaneously injected into the flank of athymic (nu/nu) mice in a proportion of $2.5 \times 10^6$ cells per animal. The animals are weighed regularly and the tumor volume is measured 3 times a week and calculated according to the ellipsoid formula V=length×width×thickness×0.5236 mm$^3$.

When the tumors reach a tumor volume of 500-1000 mm$^3$ (12-15 days after injection of the cells), the animals are treated intratumorally or intraperitoneally with the anti-CRLR, anti-RAMP2 or anti-RAMPS antibodies or a mixture composed of the anti-CRLR, anti-RAMP2 and anti-RAMP3 antibodies, the final concentration of which is 330 µg/animal, at a rate of 3 injections/week. The anti-CRLR, anti-RAMP2 and anti-RAMP3 antibodies were produced in rabbits by injection of the peptide sequences SEQ ID No. 2, 3 and 5, respectively. The groups of animals used as a control are treated in the same manner with an irrelevant antibody or a pre-immune serum.

The animals are sacrificed at varying times during the treatment (d2, d7, d11, d16 and d21), and the tumors are immediately removed and fixed in formol. They are then embedded in paraffin for the immunohistochemical studies.

One group of animals treated for 21 days receives an injection of biotinylated lectin (Biotinylated *Lycopersicon esculentum* (tomato) lectin, CliniSciences) under anesthesia. The animals are perfused with a 4% paraformaldehyde solution which makes it possible to fix the tissues in vivo. The tumors and several organs (brain, lung, heart and kidney) are removed and frozen in liquid nitrogen for histology and immunohistochemistry studies.

In Vivo Angiogenesis

Three groups of C57BL/6 mice are subcutaneously implanted with a solution of Matrigel free of growth factors (BD Biosciences).

Group (1) Matrigel alone.
Group (2) Matrigel containing 500 ng of VEGF$_{165}$ (R&D Systems, France).
Group (3) Matrigel containing 500 ng of adrenomedullin (Bachem).

After 48 hours, the animals of group (3) are separated into 3 subgroups which are treated 3 times per week, intraperitoneally, with a mixture of the anti-CRLR, anti-RAMP2 and anti-RAMP3 antibodies. The following subgroups are distinguished: subgroup (1): treated animals (25 µg/animal), subgroup (2): treated animals (100 µg/animal) and subgroup (3): treated animals (500 µg/animal).

In parallel, a 4th subgroup of animals is treated with the preimmune serum (IgG) at the dose of 500 µg/animal.

After 21 days of treatment, the animals are randomized and separated into 2 subgroups. In the first subgroup, the animals are sacrificed and the Matrigel implants are recovered and fixed in formol, and then paraffin-embedded for the histological analyses. The animals of the second subgroup are injected, under anesthesia, with dextran-FITC (Sigma, France) and sacrificed after 30 minutes. The Matrigel implants are then treated with dispase (Roche), and centrifuged at 5000 rpm at 4° C. Supernatants are recovered and the fluorescence is read at 492 (excitation)-512 nm (emission).

I.5. Western Blotting Analyses

Preparation of Protein Extracts

The cell pellets originating from U87 glial tumor cells, and the homogenates obtained from glial tumors xenografted in nude mice or from tumors from patients suffering from glioblastomas are taken up in a lysis buffer (20 mM HEPES, pH 7.9, 10 mM NaCl, 1 mM MgCl$_2$, 10% glycerol, 0.2 mM EDTA, 0.5 mM DTT, 1% protease inhibitors and 0.35% Triton X-100) and homogenized at 4° C. After centrifugation at 12 000×g for 10 minutes, the supernatant containing the proteins is recovered and the proteins are quantified by the Pierce method.

Western Blotting

The cell lysates (50 µg) are separated by 12% polyacrylamide gel electrophoresis under denaturing and reducing conditions. At the end of the migration in a 0.25 M Tris-base buffer containing 1.92M glycine and 1% SDS, the proteins are transferred onto a PVDF membrane at 1 mA/cm$^2$ for 1 h30. The membranes are saturated for 1 h at ambient temperature in PBS-5% skimmed milk.

After 2 washes (PBS-0.2% Tween 20), the membranes are incubated with agitation overnight at 4° C. in the presence of the anti-CRLR, anti-RAMP2 or anti-RAMPS antibodies diluted to 1/400 in PBS-1% skimmed milk. After 3 washes (PBS-0.2% Tween 20), the membranes are incubated for 1 h30 at ambient temperature with the peroxidase-labeled secondary antibody (ECL kit, GE Healthcare, Amersham). The signal is visualized using the chemiluminescence kit (ECL kit, GE Healthcare, Amersham).

I.6. Immunohistochemistry Studies

The various histological analyses were carried out on 6 µm frozen sections of tumors (cryostat) or paraffin-embedded sections of tumors (microtome). The sections are 30-50 µm for the tumors from mice injected with the biotinylated lectin.

The sections are deparaffinized after a xylene bath followed by 3 baths of ethanol (100%, 95% and 75%). After washing with PBS, the nonspecific sites are saturated with serum from the Vectastain kit (Abcys). The sections are then incubated overnight with the primary antibody. The various antibodies used are: anti-factor VIII (Dako, 1:300), anti-CD31 (Dako, 1:40), anti-CD34 (Zymed laboratories), anti-aSMA (Dako, 1:100), anti-NG2 (Chemicon, 1:150) and anti-desmin (Abcam, 1:50). The leukocytes and the monocytes/macrophages were detected using anti-CD45 antibodies (BD Pharmingen, 1:40) and the MOMA-2 antibody (Chemicon, 1:25).

For the labeling of the cells in apoptosis, the antibody Mab F7-26 (AbCys) was used, and for the cell proliferation, the anti-Ki67 antibody was used (Dako, 1:80).

After 3 washes with 0.1M phosphate buffer, pH 7.4, the sections are incubated at ambient temperature for 1 h30 with Dapi (Invitrogen, 1/30 000) and the fluorochrome-coupled secondary antibodies (Invitrogen: 1/250). The biotinylated lectin is visualized with the streptavidin-Alexa fluor secondary antibody (Invitrogen, 1/250). After 3 washes, the sections are covered with cover slips. The acquisitions of the photographs are carried out using a Zeiss microscope and the Leika software.

I.7. Statistical Analyses

All the experiments were repeated 3 to 4 times. The statistical analysis was carried out by means of the Anova test/S-test. The results are considered to be significant starting from $P<0.05$.

II: Results

II.1. The Anti-AMR Antibodies (Mixture of Anti-CRLR, Anti-RAMP2 and Anti-RAMP3 Antibodies) Inhibit Glial Cell Proliferation In Vitro During the characterization of the anti-adrenomedullin receptor antibodies, it was demonstrated that these antibodies are capable of inhibiting, in a dose-dependent manner, the binding of radioactive adrenomedullin "$^{125}$I-AM" to membrane preparations originating from tumor cells (FIG. 1A).

These in vitro experiments also make it possible to demonstrate the presence of an autocrine and/or paracrine loop involving adrenomedullin and its receptors CRLR, RAMP2 and RAMPS in the proliferation of tumor cells (FIG. 1B). These data also demonstrate that the mixture of anti-CRLR, anti-RAMP2 and anti-RAMP3 antibodies recognizes the adrenomedullin receptor and consequently blocks the proliferation of these cells due to the action of the adrenomedullin secreted by these same cells.

II.2. The Anti-AMR Antibodies (Mixture of Anti-CRLR, Anti-RAMP2 and Anti-RAMP3 Antibodies) Inhibit Glial Tumor Growth In Vivo The tumors developed in the athymic mice after subcutaneous injection of cell lines (U87) represent an experimental model which takes into account all the components of the tumor microenvironment.

Intratumoral Antibody Administration

Figure 2:
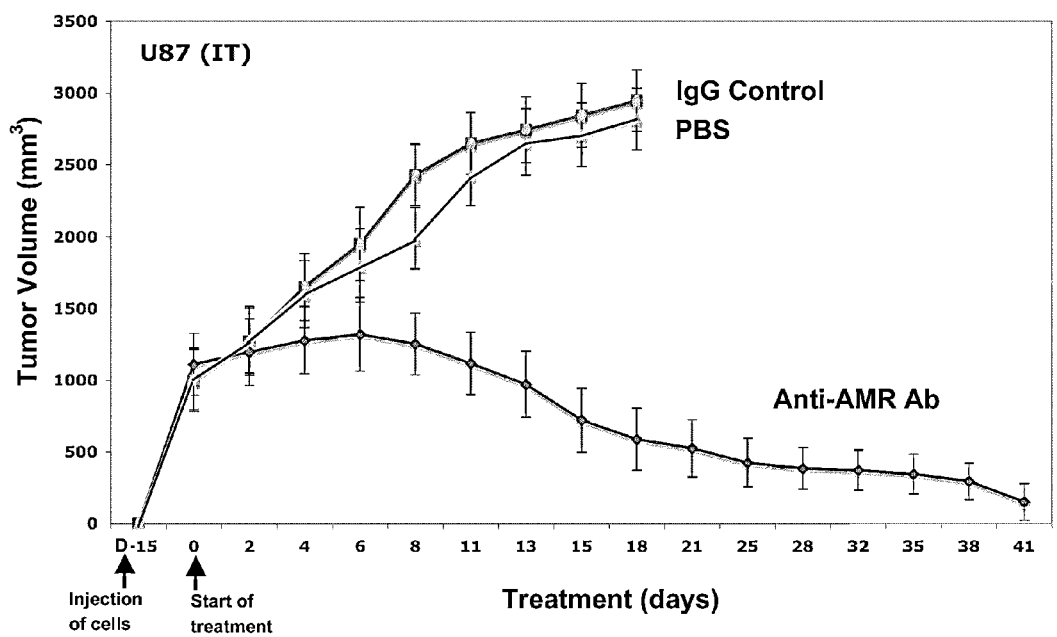
FIG. 2: Intratumoral administration of the anti-AMR antibodies inhibits tumor growth in vivo. A. Intratumoral administration of the mixture of the anti-CRLR, anti-RAMP2 and anti-RAMP3 antibodies (250 µg/animal) induces a 60-70% inhibition of xenograft tumor growth after 21 days of treatment, compared with the control mice treated with the rabbit pre-immune serum (n=10). ANOVA Test: , $p<0.01$; *, $p<0.001$. B. Photos of the control tumors and treated tumors at 16 days after treatment.
Figure 2:
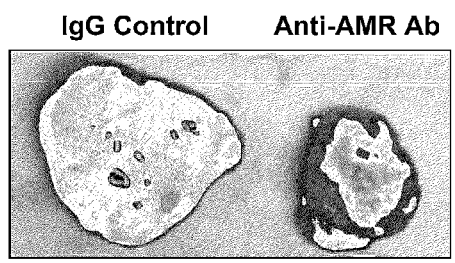

The intratumoral administration of the mixture of anti-CRLR, anti-RAMP2 and anti-RAMP3 antibodies induces a 60-70% inhibition of xenograft tumor growth after 21 days of treatment (FIG. 2 A). After 16 days of treatment, it was observed that the tumors of animals treated with the anti-AMR antibodies appeared pale, translucent and less vascularized (FIG. 2 B). In contrast, the control animals exhibit highly vascularized large tumors. These important effects observed in vivo suggest that, in addition to an action on tumor cell proliferation, the treatment with the anti-AMR antibodies disrupts a fundamental mechanism essential for tumor growth.

Intraperitoneal Antibody Administration

In order to evaluate the therapeutic effect of the anti-AMR antibodies on tumor growth in vivo, the anti-AMR antibodies were administered intraperitoneally.

Figure 3:
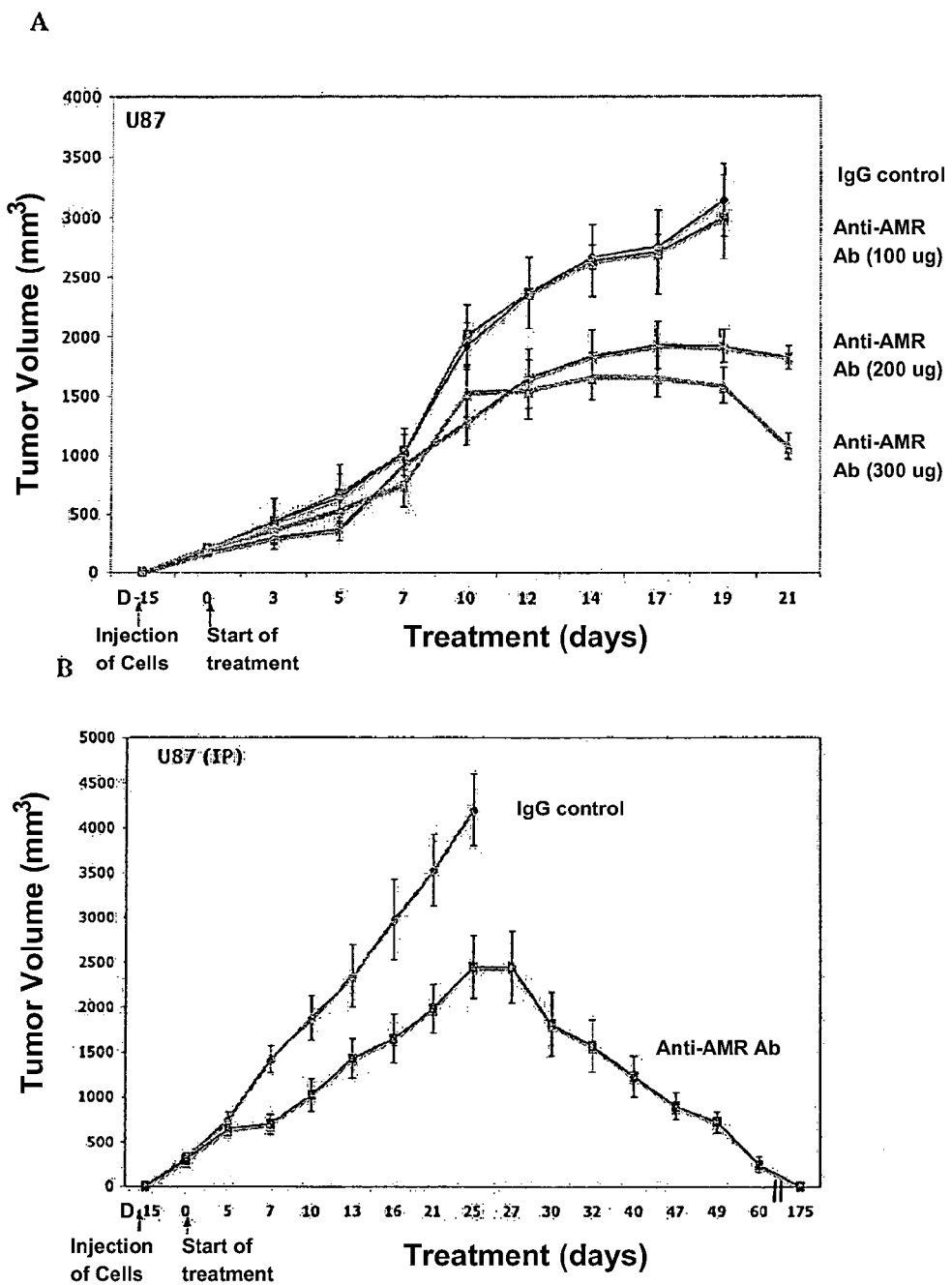
FIG. 3: Intraperitoneal administration of the anti-AMR antibodies inhibits tumor growth in vivo. A. With the aim of establishing intraperitoneal treatment, various doses (100, 200 and 300 µg) of the mixture of anti-AMR antibodies were tested in mice xenografted with the U87 line (n=8). B. Intraperitoneal injection of 330 µg/mouse of a mixture of anti-CRLR, anti-RAMP2 and anti-RAMPS antibodies inhibits tumor growth and increases the survival of the mouse up to 175 days compared with the mice treated with the control IgGs, which died between 20-25 days after treatment (n=10).

Four groups, each of 8 mice, were treated 3 times per week with control IgGs (330 µg) and anti-AMR (100, 200, 330 µg) (FIG. 3 A).

These results show a dose-dependent inhibition of glial tumor growth after treatment with the anti-AMR antibodies. The concentration of 330 µg was adopted for the remainder of the studies, with the same injection protocol.

The intraperitoneal treatment shows a very large inhibition of glial tumor growth and a much longer survival of the mice treated with the anti-AMR antibodies compared with the mice treated with the control IgGs (FIG. 3 B).

The intraperitoneal treatment also shows a very large inhibition of glial tumor growth and a much longer survival of the mice treated with the mixture of the three anti-CRLR, anti-RAMP2 and anti-RAMPS antibodies compared with the mice treated with a single anti-CRLR, anti-RAMP2 or anti-RAMPS antibody (FIG. 3 C).

II.3. The Anti-AMR Antibody (Mixture of Anti-CRLR, Anti-RAMP2 and Anti-RAMP3 Antibodies) Destabilize Tumor Vascularization In Vivo In order to better understand the mechanisms involved in tumor regression after treatment with the anti-AMR (anti-CRLR/anti-RAMP2/anti-RAMP3) antibodies, histological analyses were carried out in tumor sections. The use of endothelial markers such as CD31 or von Willebrand (vWF) factor attest to a profound disorganization or even destabilization of the vascular architecture resulting in a decrease in vessel size.

Figure 4:
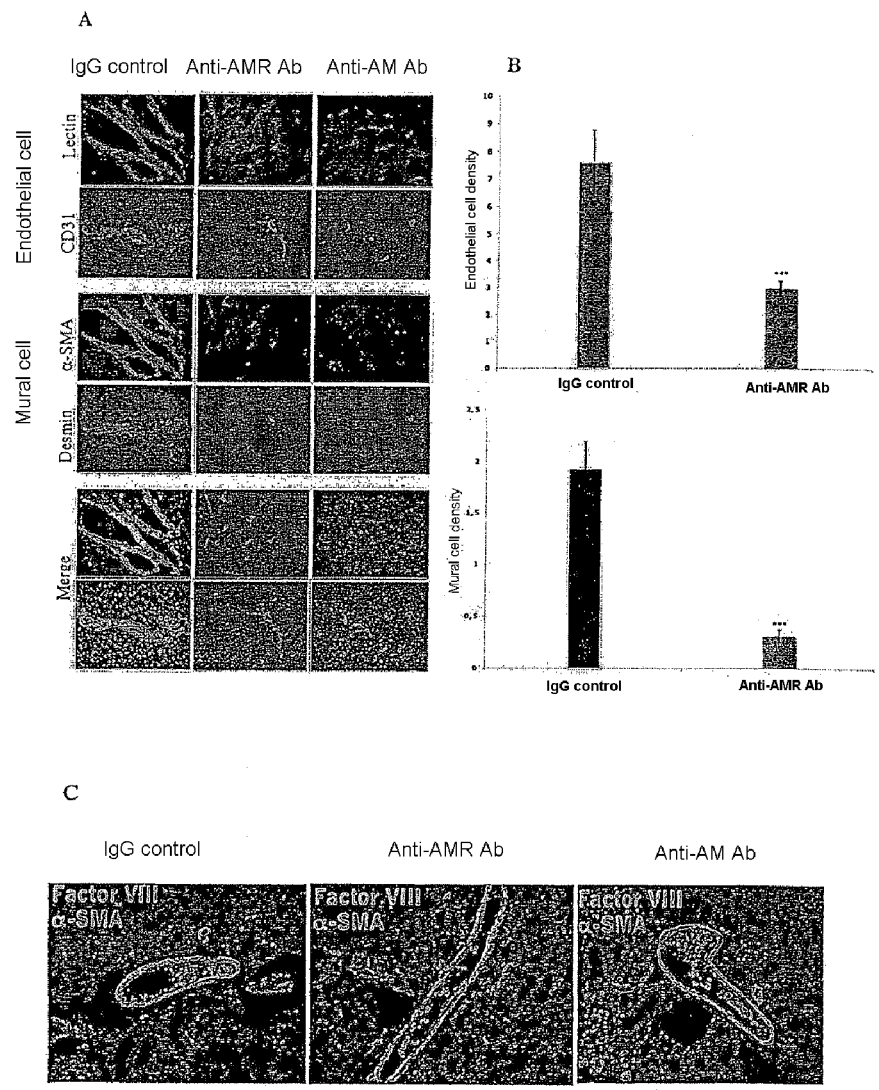
FIG. 4: The anti-AMR antibodies destabilize the tumor vascularization in vivo. A. The histological analyses carried out on sections of tumors from mice having received biotinylated lectin (marker having a high affinity for endothelial cells) by injection, and after visualization with streptavidin, show destabilization of the vascular architecture resulting in a decrease in the size of the vessels compared with the control tumors. The immunohistochemical study with pericyte markers (desmin or a-SMA) shows a very significant decrease in or even a disappearance of the pericytes at the level of the vessels of the treated tumors compared with the control tumors. B. The quantification of the vascularization and the cell density (endothelial cells compared with pericytes) between the two groups of animals shows a considerable decrease in the number of endothelial cells and of pericytes labeled per unit surface area in the tumors treated with the anti-AMR antibodies. ANOVA Test: , $p<0.01$; *, $p<0.001$. C. The labeling by immunohistochemistry of the endothelial cells (FvIII)/pericytes (a-SMA) shows the absence of effects with the treatment with the anti-AMR antibodies systemically, on the "normal" vascular architecture in the mouse kidney.

Injection of the biotinylated lectin (marker having a high affinity for endothelial cells) in mice 15 minutes before sacrifice shows a stable and functional vascularization in the animals treated with the control IgGs, whereas vascular disorganization was observed in the animals treated with the anti-AMR antibodies. Interestingly, the immunohistochemical study with pericyte markers (NG2, desmin or α-SMA) shows a very significant decrease in, or even disappearance of, the pericytes around the vessels of the treated tumors compared with the control tumors (FIG. 4 A). Quantification of the vascularization and the cell density (endothelial cells compared with pericytes) between the two groups of animals shows a significant decrease in the treated tumors (FIG. 4 B). The experiments thus suggest that adrenomedullin regulates covering of the vessels by pericytes and that the anti-AMR antibodies are capable of blocking pericyte recruitment at the vessels. This reveals that the anti-AMR antibodies induce a regression of tumor vascularization, probably through destabilization of the vessels after loss of the supporting cells, the pericytes.

Immunohistochemical analysis of the vascularization of various organs (kidney, heart, lung, etc.) by means of colabeling of the endothelial/pericyte cells in the various groups of mice treated with the anti-AMR antibodies and the mice treated with the control IgGs shows the absence of effects of the treatment on the non-tumor vascular architecture (FIG. 4 C). These results reveal that the anti-AMR antibodies act only on the tumor without however having effects on the vascularization of the various organs of the mouse.

Figure 5:
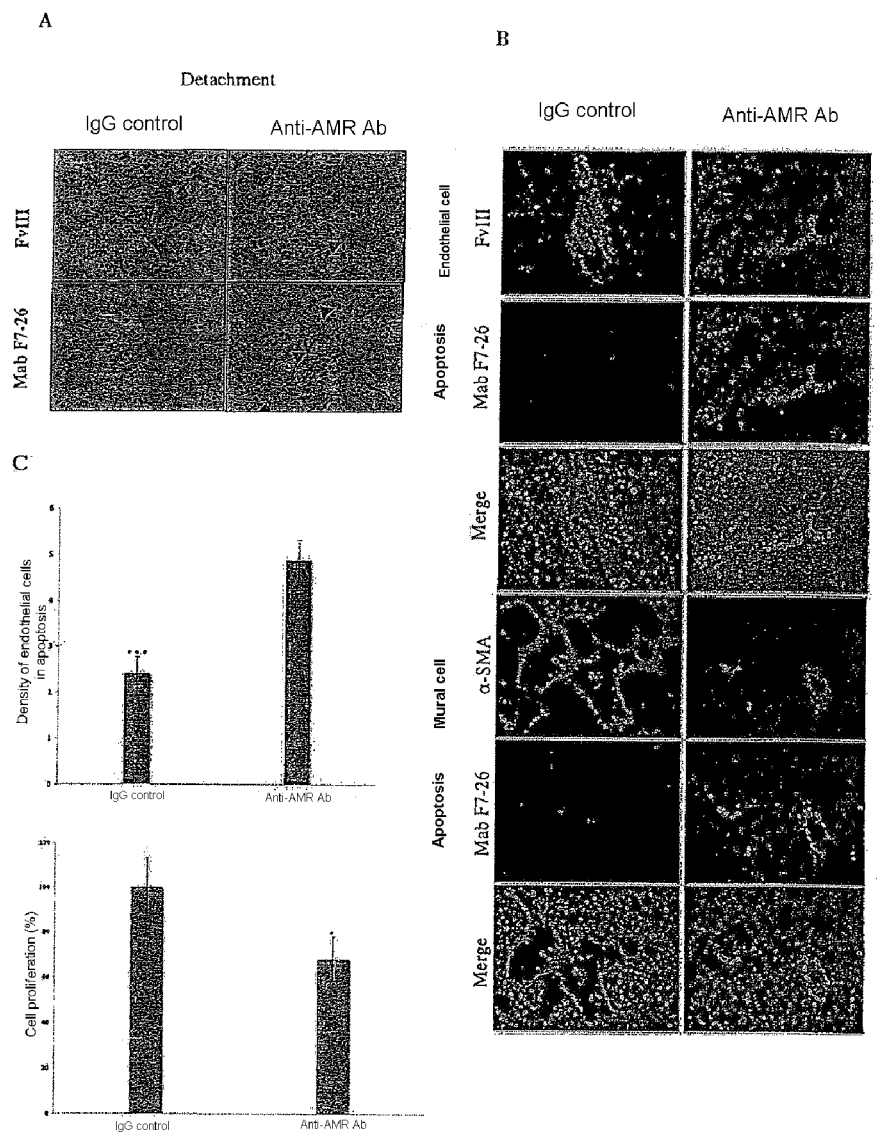
FIG. 5: The anti-AMR antibodies induce apoptosis of the endothelial cells and of the pericytes. A. Labeling using the F7-26 Mab antibody shows that the endothelial cells detached from the endothelium, under the effect of the absence of pericytes, caused by the treatment with the anti-AMR antibodies, undergo apoptosis. B. Labeling of the endothelial cells (FvIII) and of the pericytes (a-SMA) in parallel with labeling using the F7-26 Mab antibody shows that the pericytes, like the endothelial cells, are in a state of apoptosis in the tumors treated with the anti-AMR antibodies compared with the control tumors. C. The quantification of the density of endothelial cells undergoing apoptosis shows a significant increase in the tumors treated with the anti-AMR antibodies compared with the control tumors. The labeling of general cell proliferation on the 16th day of treatment shows only a decrease of 25-35% in the treated tumors compared with the control tumors. *=$P<0.05$, =$P<0.01$, *=$P<0.001$.

Pericytes contribute to the angiogenic process by means of an effect on extracellular matrix synthesis or degradation, and to vascular wall stability by participating in basal membrane assembly, and also appear to be a paracrine regulatory factor suppressing endothelial cell proliferation and migration (Sato and Rifkin, *J. Cell Biol.,* 1989, 109:309-15; Benjamin et al., *Development,* 1998, 125:1591-8). The architecture of the vascular tree is controlled and stabilized by blood flow, but also by the interactions which are established between endothelial cells, pericytes, smooth muscle cells and extracellular matrix (Allt and Lawrenson, *Cells Tissues Organs,* 2001, 169:1-11). The use of Mab F7-26 demonstrating the presence of apoptosis shows that the endothelial cells detached from the endothelium, owing to the absence of the pericytes, caused by the treatment with the anti-AMR antibodies, undergo apoptosis (FIG. 5 A). This same labeling was observed for the rare pericyte cells present in the treated tumors (FIG. 5 B). On the other hand, the labeling of the general cell proliferation on day 16 of treatment shows only a 25-35% decrease in the treated tumors compared with the control tumors (FIG. 5 C). These results emphasize the potential role of adrenomedullin on pericyte recruitment, thus implicating this cell type as an important functional component of tumor vascularization.

II.4. Effect of Intraperitoneal Treatment with the Anti-AMR Antibodies (Mixture of Anti-CRLR, Anti-RAMP2 and Anti-RAMP3 Antibodies)

Figure 6:
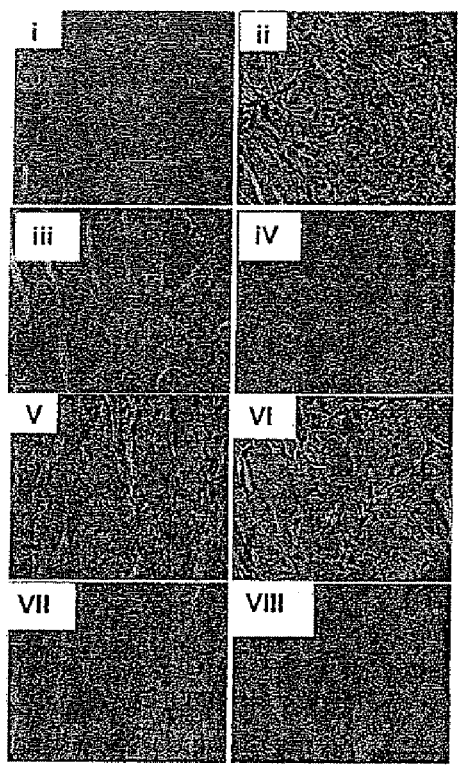
FIG. 6: Adrenomedullin activates cell migration in an autocrine/paracrine manner during the angiogenic process in vivo. A. Immunohistochemical labeling with hematoxylin/eosin on sections of paraffin-embedded Matrigel implants shows considerable cell invasion in the Matrigel containing the adrenomedullin compared with that which contains no factor. Treatment with anti-AMR antibody mixture induces a decrease in recruitment of the circulating cells into the Matrigel implants, in a dose-dependent manner (n=10 per group). (I): Matrigel alone, (II): Matrigel+AM (500 ng), (III): Matrigel+VEGF (500 ng), (IV): Matrigel+AM (500 ng)+anti-AM Ab (500 µg), (V): treatment with the control IgGs (500 µg), (VI), (VII) and (VIII): treatment with the anti-AMR antibodies (25 µg, 100 and 500 µg). B. Quantification of the number of cells per unit surface area of the Matrigel sections. *=$P<0.05$, =$P<0.01$, *=$P<0.001$. (N=10).
Figure 6:
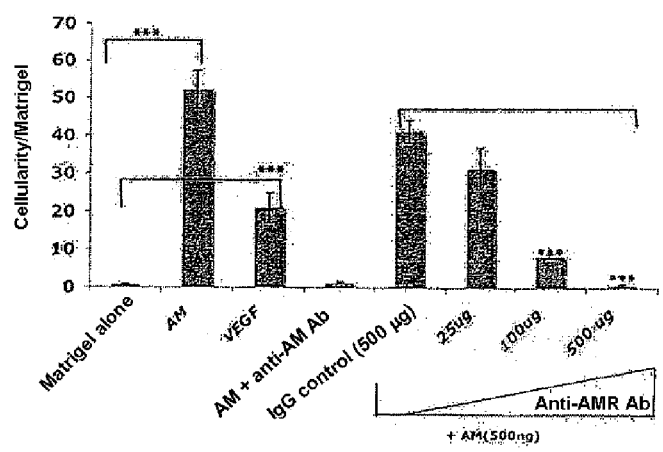

The in vivo angiogenesis test using Matrigel free of growth factors and supplemented only with adrenomedullin, injected into C57BL/6 mice subcutaneously, is a good model for studying the effect of the presence of this factor on the mobilization of the various cell types. Staining with hematoxylin/eosin on histological sections shows cell invasion within the Matrigel containing the adrenomedullin, in comparison with the Matrigel with no factor. Moreover, the cell density is higher if a comparison is made with the Matrigel containing VEGF (FIG. 6 A). In order to evaluate the role of the anti-AMR antibodies (anti-CRLR/anti-RAMP2/anti-RAMP3) on the recruitment of circulating cells, the effect of intraperitoneal treatment with these antibodies was tested. The results show that the treatment with the anti-AMR antibodies induces a decrease in the recruitment of circulating cells in the Matrigel implants, in a dose-dependent manner (FIGS. 6 A and B). The specificity of the anti-AMR antibodies is demonstrated in comparison with the treatment using the pre-immune IgGs.

II.5. Effect of Adrenomedullin on the Angiogenesis Process In Vivo

Figure 7:
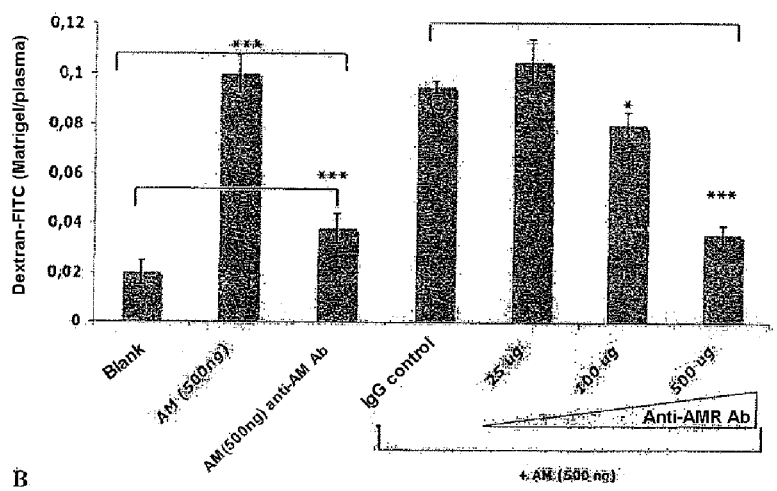
FIG. 7: Effect of adrenomedullin on the angiogenesis process in vivo. A. The assaying of dextran-FITC injected into mice having subcutaneous Matrigel implants shows a considerable amount of dextran in the Matrigel containing the adrenomedullin compared with the control. The amount of FITC-dextran decreases in a dose-dependent manner in the mice treated with the anti-AMR antibodies compared with the mice treated with the control IgGs. ANOVA Test: , $p<0.01$; *, $p<0.001$. B. Labeling using the anti-CD31, anti-FvIII, anti-CD34 (endothelial cells and precursors thereof), anti-aSMA (pericytes), anti-CD45 and MOMA-2 (leukocytes, monocytes/macrophages) antibodies shows the presence of these various cell types in the Matrigel implants. Labeling with the anti-CRLR, anti-RAMP2 and anti-RAMP3 antibodies shows coexpression of the adrenomedullin receptors with the various labelings used above.
Figure 7:
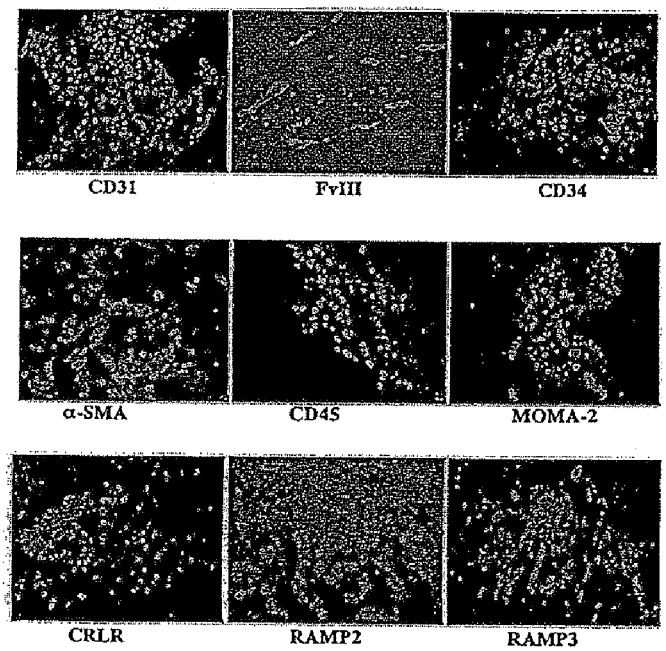

The injection of dextran-FITC in C57BL/6 mice having received, subcutaneously, Matrigel optionally containing adrenomedullin, 30 minutes before sacrifice of the animal, makes it possible to study the effect of adrenomedullin on angiogenesis in vivo. Fluorescent FITC assaying shows a large amount of dextran in the Matrigel containing adrenomedullin compared with the control, attesting to the fact that functional angiogenesis has been set up under the effect of the adrenomedullin (FIG. 7 A). The amount of FITC-dextran decreases in a dose-dependent manner in the mice treated with the anti-AMR antibodies compared with the mice treated with the control IgGs.

Blood vessel formation is a process which uses several cell types: endothelial cells, which coat the vessel wall; pericytes, which stabilize these walls; and circulating cells (inflammatory cells, endothelial cell precursors and mesenchymal cells). Labeling using various markers of endothelial cells and their precursors (anti-CD31, anti-FvIII, anti-CD34), of pericytes (anti-aSMA, anti-desmin, anti-NG2) and of inflammatory cells (anti-CD45 and MOMA-2) made it possible to identify the various cell types attracted by the presence of adrenomedullin (FIG. 7 B). Labeling with the anti-CRLR, anti-RAMP2 and anti-RAMPS antibodies made it possible to differentiate the cell populations expressing adrenomedullin receptors and, consequently, recruited into the Matrigel under the paracrine effect of adrenomedullin. On the other hand, the results also reveal the presence of cells which do not express these receptors and which are probably recruited into the Matrigel under the effect of other factors which may be released by the various cells after they come into contact with the adrenomedullin.

These results show that adrenomedullin is involved, via an autocrine/paracrine effect, in various steps of intratumor neoangiogenesis, such as cell migration, invasion and differentiation, via its receptors. Thus, blocking adrenomedullin receptors (AMRs) appears to be sufficient to inhibit tumor growth.

II.6. Effect of the Treatment with the Anti-AMR Antibodies (Mixture of Anti-CRLR, Anti-RAMP2 and Anti-RAMP3 Antibodies) on Various Tumor Models The various results obtained define adrenomedullin as a factor involved in tumor angiogenesis.

With the aim of establishing an anticancer therapy, the effect of the treatment with the anti-AMR (anti-CRLR/anti-RAMP2/anti-RAMP3) antibodies on other tumor models, such as lung, colon, kidney, breast and skin cancer, was verified.

Figure 8:
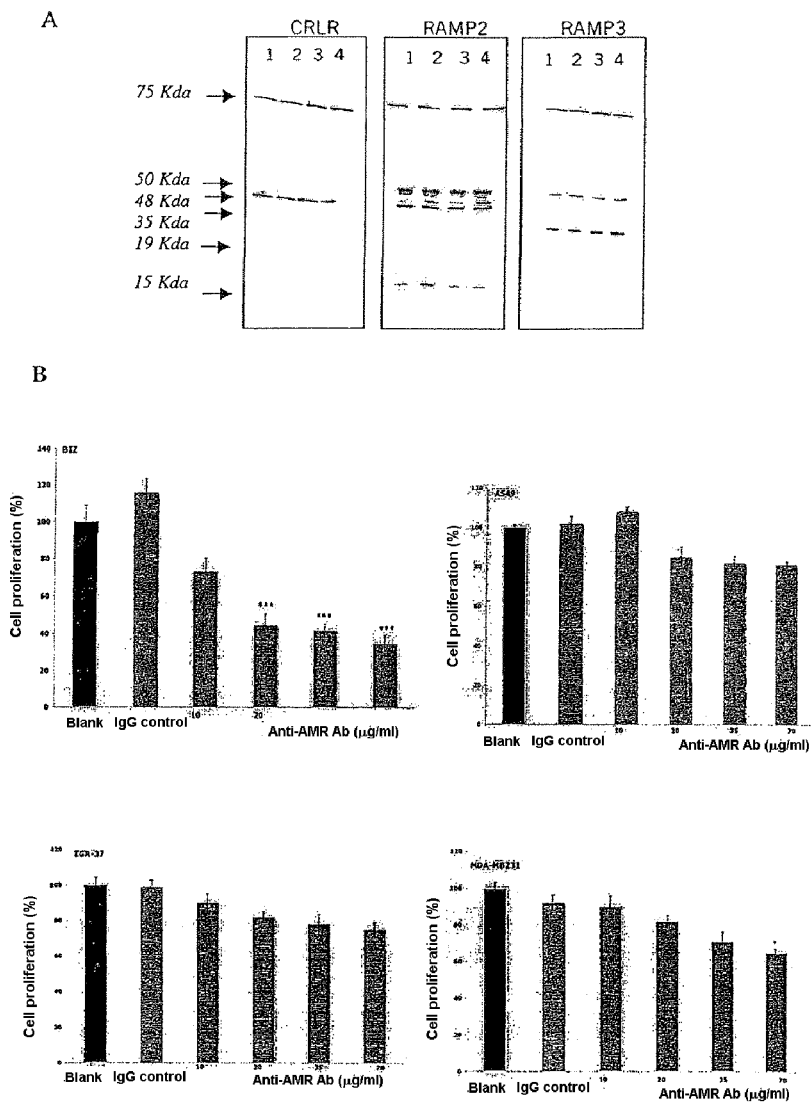
FIG. 8: Adrenomedullin as therapeutic target. Western blotting analysis on protein extracts of the tumor lines A549 (1), MDA 231 (2), IGR37 (3) and BiZ (4) shows the various protein forms of adrenomedullin receptors (A). The CRLR/RAMP2 and CRLR/RAMP3 complexes ($\approx$75 Kda), CRLR (48 Kda), RAMP2 (35 Kda=glycosylated form, 15 Kda=native form) and RAMP3 (19 Kda=native form). The homodimer forms RAMP2/RAMP2 and RAMP3/RAMP3 were also detected ($\approx$50 Kda). The in vitro proliferation test shows that the treatment with the anti-AMR antibodies (mixture of the three anti-CRLR, anti-RAMP2 and anti-RAMP3 antibodies) inhibits cell proliferation by up to 75% in the kidney cell line (BIZ) (B). In the other lines, A549, IGR-37 and MDA-MB 231, the inhibition of proliferation is 5-30% (B). ANOVA Test: *, $p<0.05$; , $p<0.01$; *, $p<0.001$. The intraperitoneal treatment with the anti-AMR antibodies (330 µg/animal) in the mice xenografted with HT29 cells (C) and A549 cells (D) shows a considerable inhibition of tumor growth, compared with the mice treated with the pre-immune serum (N=10). ANOVA Test: , p<0.01; *, p<0.001.
Figure 8:
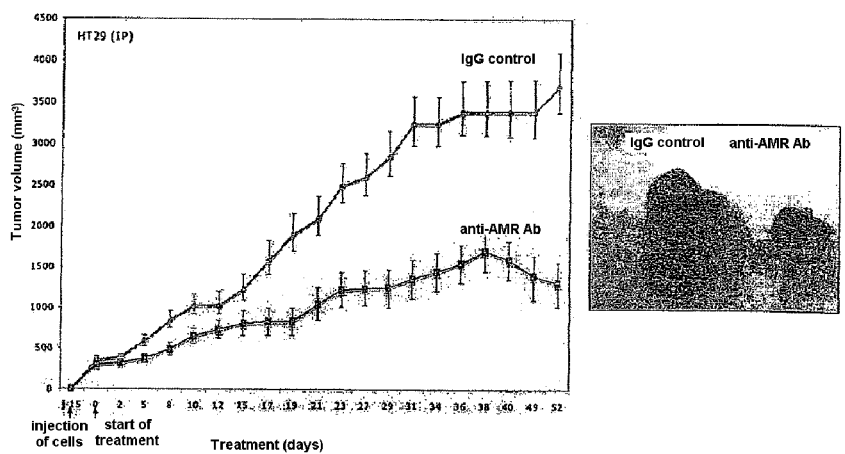
Figure 8:
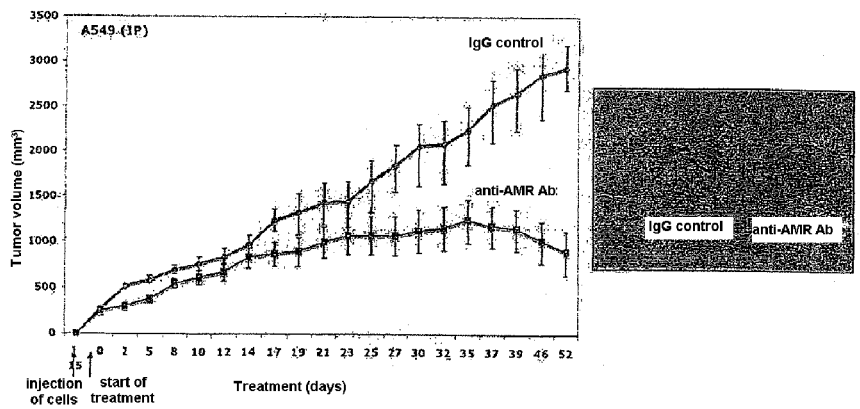

Analysis by the western blotting technique carried out on protein extracts of the various tumor lines, A549 for lung cancer, HT29 for colon cancer, A498, Caki 1,2 and BIZ for kidney cancer, MDA-MB-231 for breast cancer and IGR for skin cancer, shows the presence of the various proteins constituting adrenomedullin receptors, CRLR, RAMP2 and RAMPS (FIG. 8 A).

The in vitro study of the effect of the anti-AMR (anti-CRLR/anti-RAMP2/anti-RAMP3) antibodies on the proliferation of these various lines shows an inhibition of proliferation which reaches 70% at 70 µg/ml after 6 days of treatment in the kidney line, BIZ (FIG. 8 B). As regards the other lines, namely A549, IGR-37 and MDA-MB231, the inhibition of cell proliferation is approximately 30% with the same antibody concentration (FIG. 8 B). Moreover, these results show that in vitro proliferation of the BIZ line requires the presence of adrenomedullin, in comparison with the other lines studied.

The investigation was continued in vivo in nude mice (Balb-c nu/nu). For this, heterotopic xenografts were developed subcutaneously.

Intraperitoneal treatment with the anti-AMR antibodies in the mice xenografted with the HT29 (FIG. 8 C) and A549 (FIG. 8 D) lines shows considerable inhibition of tumor growth compared with the mice treated with the pre-immune serum. These first observations suggest good general tolerance of the treatment with the anti-AMR antibodies (weight curve and general condition of the mice treated). The tumors of the treated mice are 3 times smaller in volume than the control tumors and also appear to be less vascularized. These results demonstrate the important role that adrenomedullin must play in the development of malignant tumors. The preliminary immunohistochemistry studies on sections of colon xenografts, by labeling with factor VIII and CD31 for endothelial cells and α-SMA and desmin for pericytes, show a very substantial effect of the anti-AMR antibodies on tumor angiogenesis.

II.7. Effect of the Anti-AMR (Anti-CRLR/Anti-RAMP2/Anti-RAMP3) Antibodies on Glial Tumor Growth in Orthotopically Developed Xenografts Three groups, each of 10 mice, were injected intracerebrally with one million U87 cells. Ten days later, the mice, weakened because of the disease, undergo a weight loss (14 g±2) compared with the normal mice without injection of cells (20 g±2). The mice are separated into several groups, and received, 3 times per week, intraperitoneally, 330 µg of the control IgGs or of the anti-adrenomedullin (anti-AM) antibody or of the anti-adrenomedullin receptor (anti-AMR) antibodies (FIG. 9 A).

Figure 9:
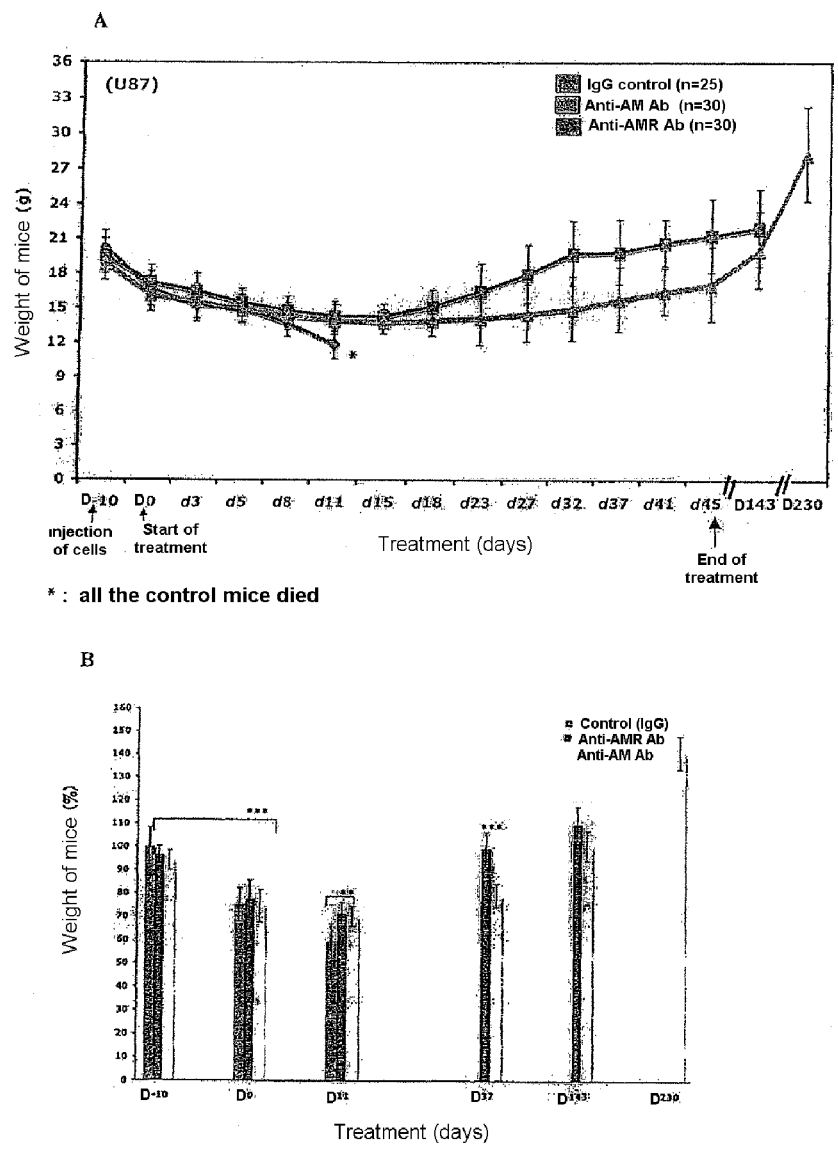
FIG. 9: The anti-AM or anti-AMR antibodies inhibit the tumor growth of glial xenografts developed orthotopically. A. The mice having received U87 cells by intracerebral injection show a considerable increase in weight after 5-10 days of intraperitoneal treatment with the anti-AM or anti-AMR antibodies (330 µg/animal). These mice also show a prolonged survival that is about 12 times greater than the mice treated with the pre-immune serum (N=10). B. The weight of the mice, expressed as a percentage, shows the extent of the weight variations after the injection of the U87 tumor cells orthotopically and also during the treatment. ANOVA Test: , p<0.01; *, p<0.001.

In the mice having received the control IgGs by injection, survival was 5-10 days after treatment with a spectacular drop in their weight (FIG. 9 B).

On the other hand, in the groups of the mice treated with the anti-AM or anti-AMR antibodies, a weight gain was observed in 60 to 70% of said mice a few days after the treatment, with survival being extended beyond 230 days (FIG. 9 B).

Finally, in the treated mice, no metastasis was observed in the organs after sacrifice of the animal.

The invention claimed is:

1. A mixture of at least three antibodies and/or fragments of said antibodies, which bind to three proteins that form adrenomedullin receptors, wherein each antibody and/or antibody fragment binds to a different protein, wherein the three proteins are calcitonin receptor like receptor (CRLR), receptor activity-modifying protein 2 (RAMP2) and receptor activity-modifying protein 3 (RAMP3), and wherein:
- one of the at least three antibodies and/or fragments of said antibodies binds to an extracellular domain of CRLR and can be obtained by immunization of an animal with a peptide sequence selected from the group consisting of SEQ ID No. 1 and SEQ ID No. 2,
- one of the at least three antibodies and/or fragments of said antibodies binds to an extracellular domain of RAMP2 and can be obtained by immunization of an animal with a peptide sequence selected from the group consisting of SEQ ID No. 3 and SEQ ID No. 4, and/or
- one of the at least three antibodies and/or fragments of said antibodies binds to an extracellular domain of RAMP3 and can be obtained by immunization of an animal with a peptide sequence selected from the group consisting of SEQ ID No. 5 and SEQ ID No. 6.

2. The mixture as claimed in claim 1, wherein said antibodies bind to an extracellular domain of each of said proteins.

3. The mixture as claimed in claim 1, wherein said antibodies are polyclonal antibodies.

4. A pharmaceutical composition comprising the mixture of claim 1, and at least one pharmaceutically acceptable vehicle.

5. An antibody, which binds to an extracellular domain of CRLR, wherein said antibody can be obtained by immunization of an animal with a peptide of sequence SEQ ID No. 1.

6. An antibody, which binds to an extracellular domain of RAMP2, wherein said antibody can be obtained by immunization of an animal with a peptide of sequence SEQ ID No. 4.

7. An antibody, which binds to the extracellular domain of RAMP3, wherein said antibody can be obtained by immunization of an animal with a peptide of sequence SEQ ID No. 6.

8. A method for obtaining an antibody, which binds to an extracellular domain of CRLR comprising a step of immunizing an animal with a peptide sequence consisting of SEQ ID No. 1.

9. A method for obtaining an antibody, which binds to the extracellular domain of RAMP2 comprising a step of immunizing an animal with a peptide sequence consisting of SEQ ID No. 4.

10. A method for obtaining an antibody, which binds to the extracellular domain of RAMP3 comprising a step of immunizing an animal with a peptide sequence consisting of SEQ ID No. 6.

11. A method of treating a solid tumor in a subject comprising administering to said subject a mixture according to claim 1, wherein said solid tumor is selected from the group consisting of glioblastoma, lung, colon, kidney, breast and skin tumors.

12. The method according to claim 11, wherein said solid tumor is selected from the group consisting of glioblastoma, lung and colon tumors.

13. The mixture as claimed in claim 1, wherein:
- one of the at least three antibodies and/or fragments of said antibodies binds to an extracellular domain of CRLR and can be obtained by immunization of an animal with a peptide sequence selected from the group consisting of SEQ ID No. 1 and SEQ ID No. 2,
- one of the at least three antibodies and/or fragments of said antibodies binds to an extracellular domain of RAMP2 and can be obtained by immunization of an animal with a peptide sequence selected from the group consisting of SEQ ID No. 3 and SEQ ID No. 4, and
- one of the at least three antibodies and/or fragments of said antibodies binds to an extracellular domain of RAMP3 and can be obtained by immunization of an animal with a peptide sequence selected from the group consisting of SEQ ID No. 5 and SEQ ID No. 6.

14. A method of treating a solid tumor in a subject comprising administering to said subject a mixture according to claim 13, wherein said solid tumor is selected from the group consisting of glioblastoma, lung, colon, kidney, breast and skin tumors.

15. The method according to claim 14, wherein said solid tumor is selected from the group consisting of glioblastoma, lung and colon tumors.

* * * * *

SEQUENCE LISTING

<160> NUMBER OF SEQ ID NOS: 6

<210> SEQ ID NO 1
<211> LENGTH: 25
<212> TYPE: PRT
<213> ORGANISM: Artificial Sequence
<220> FEATURE:
<223> OTHER INFORMATION: Peptide derived from fragment S6-K30 of the hCRLR protein

<400> SEQUENCE: 1

Ser Pro Glu Asp Ser Ile Gln Leu Gly Val Thr Arg Asn Lys Ile Met
1               5                   10                  15

Thr Ala Gln Tyr Glu Ala Tyr Gln Lys
            20                  25

<210> SEQ ID NO 2
<211> LENGTH: 31
<212> TYPE: PRT
<213> ORGANISM: Artificial Sequence
<220> FEATURE:
<223> OTHER INFORMATION: Peptide derived from fragment P68-R98 of the hCRLR protein

<400> SEQUENCE: 2

Pro Asp Tyr Phe Gln Asp Phe Asp Pro Ser Glu Lys Val Thr Lys Ile
1               5                   10                  15

Ala Asp Gln Asp Gly Asn Trp Phe Arg His Pro Ala Ser Asn Arg
            20                  25                  30

<210> SEQ ID NO 3
<211> LENGTH: 23
<212> TYPE: PRT
<213> ORGANISM: Artificial Sequence
<220> FEATURE:
<223> OTHER INFORMATION: Peptide derived from fragment K59-K81 of the hRAMP2 protein

<400> SEQUENCE: 3

Lys Asn Tyr Glu Thr Ala Val Gln Phe Ala Trp Asn His Tyr Lys Asp
1               5                   10                  15

Gln Met Asp Pro Ile Glu Lys
            20

<210> SEQ ID NO 4
<211> LENGTH: 28
<212> TYPE: PRT
<213> ORGANISM: Artificial Sequence
<220> FEATURE:
<223> OTHER INFORMATION: Peptide derived from fragment R91-R118 of the hRAMP2 protein

<400> SEQUENCE: 4

Arg Pro Tyr Ser Thr Leu Arg Asp Ala Leu Glu His Phe Ala Glu Leu
1               5                   10                  15

Phe Asp Leu Gly Phe Pro Asn Pro Leu Ala Glu Arg
            20                  25

<210> SEQ ID NO 5
<211> LENGTH: 22
<212> TYPE: PRT
<213> ORGANISM: Artificial Sequence
<220> FEATURE:
<223> OTHER INFORMATION: Peptide derived from fragment L34-K55 of the hRAMP3 protein

```
<400> SEQUENCE: 5

Leu Glu Arg Leu Pro Leu Ala Gly Lys Ala Phe Ala Asp Met Met Gly
1               5                   10                  15

Lys Val Asp Val Trp Lys
            20

<210> SEQ ID NO 6
<211> LENGTH: 22
<212> TYPE: PRT
<213> ORGANISM: Artificial Sequence
<220> FEATURE:
<223> OTHER INFORMATION: Peptide derived from fragment G91-E112 of the
      hRAMP3 protein

<400> SEQUENCE: 6

Gly Phe Ile Thr Gly Ile His Arg Gln Phe Phe Ser Asn Ala Thr Val
1               5                   10                  15

Asp Arg Val His Leu Glu
            20
```